United States Patent
Ng et al.

(10) Patent No.: US 9,044,356 B2
(45) Date of Patent: Jun. 2, 2015

(54) ABSORBENT ARTICLE HAVING ENHANCED LEAKAGE PROTECTION

(75) Inventors: Meijia Ng, Singapore (SG); SangWook Lee, Seongnam-si (KR); YeinSze Ong, Singapore (SG); DooHong Kim, Seoul (KR); Priscilla Eng Choo Goh, Singapore (SG); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 584 days.

(21) Appl. No.: 13/111,155

(22) Filed: May 19, 2011

(65) Prior Publication Data

US 2012/0296303 A1 Nov. 22, 2012

(51) Int. Cl.
*A61F 13/15* (2006.01)
*A61F 13/20* (2006.01)
*A61F 13/472* (2006.01)
*A61F 13/475* (2006.01)
*A61F 13/511* (2006.01)

(52) U.S. Cl.
CPC ..... *A61F 13/47263* (2013.01); *A61F 13/51104* (2013.01); *A61F 13/47272* (2013.01); *A61F 13/4752* (2013.01)

(58) Field of Classification Search
USPC .......... 604/385.01, 385.19, 361, 364, 385.11, 604/385.17, 385.201
See application file for complete search history.

(56) References Cited

U.S. PATENT DOCUMENTS

| 3,371,668 A | 3/1968 | Johnson |
| 3,460,536 A | 8/1969 | Champaigne, Jr. |
| 3,814,101 A | 6/1974 | Kozak |

(Continued)

FOREIGN PATENT DOCUMENTS

| AU | 149020 S | 1/2012 |
| FR | 2915372 A1 | 10/2008 |

(Continued)

OTHER PUBLICATIONS

Abstract of Chinese Patent—CN1247733, Mar. 22, 2000, 1 page.

(Continued)

*Primary Examiner* — Jacqueline Stephens
(74) *Attorney, Agent, or Firm* — Dority & Manning, P.A.

(57) ABSTRACT

An absorbent article that is capable of inhibiting leakage of a fluid insult is provided. The absorbent article contains a fluid-shrinkable member, topsheet, and a base pad that includes a baffle and an absorbent core positioned between the topsheet and the baffle. The fluid-shrinkable member extends in a longitudinal direction of the article so that at least a portion of the member is located adjacent to an end of the topsheet. At least a portion of the end of the topsheet remains generally unbonded to the baffle. Thus, when the fluid-shrinkable member contracts upon contacting a fluid insult, the end of the topsheet can rise outwardly from the plane of the absorbent article. The raised area creates a barrier to the leakage of fluids from the center of the article towards its end. In certain embodiments, contraction of the fluid-shrinkable member can also cause an outer region of the topsheet to rise outwardly from the plane of the absorbent article to create a barrier to the leakage of fluids from the center of the article towards the side edge. Notably, because such barriers are generally created only after contact with a fluid insult, their effectiveness is not diminished through use of the article prior to the insult.

20 Claims, 8 Drawing Sheets

(56) References Cited

U.S. PATENT DOCUMENTS

| | | | |
|---|---|---|---|
| 3,881,490 A | 5/1975 | Whitehead et al. | |
| D240,562 S | 7/1976 | Whitehead et al. | |
| D247,370 S | 2/1978 | Whitehead | |
| 4,079,739 A | 3/1978 | Whitehead | |
| 4,315,507 A | 2/1982 | Whitehead et al. | |
| 4,359,938 A | 11/1982 | Koren | |
| 4,447,240 A | 5/1984 | Ito et al. | |
| D276,072 S | 10/1984 | Whitehead | |
| D276,073 S | 10/1984 | Whitehead | |
| 4,533,357 A | 8/1985 | Hall | |
| 4,640,859 A | 2/1987 | Hansen et al. | |
| 4,798,603 A | 1/1989 | Meyer et al. | |
| 4,801,494 A | 1/1989 | Datta et al. | |
| 4,809,493 A | 3/1989 | Genba et al. | |
| 4,834,733 A | 5/1989 | Huntoon et al. | |
| 4,892,534 A | 1/1990 | Datta et al. | |
| 4,908,026 A | 3/1990 | Sukiennik et al. | |
| 5,074,856 A | 12/1991 | Coe et al. | |
| 5,181,563 A | 1/1993 | Amaral | |
| 5,248,309 A | 9/1993 | Serbiak et al. | |
| 5,397,316 A | 3/1995 | LaVon et al. | |
| 5,415,640 A | 5/1995 | Kirby et al. | |
| 5,429,630 A | 7/1995 | Beal et al. | |
| 5,614,295 A | 3/1997 | Quincy, III et al. | |
| 5,628,097 A | 5/1997 | Benson et al. | |
| D392,736 S | 3/1998 | Erickson | |
| 5,912,194 A | 6/1999 | Everhart et al. | |
| D425,985 S | 5/2000 | Velazquez et al. | |
| D426,303 S | 6/2000 | Weyenberg | |
| 6,093,871 A | 7/2000 | Takai et al. | |
| D430,292 S | 8/2000 | Orschel et al. | |
| 6,231,555 B1 | 5/2001 | Lynard et al. | |
| 6,262,331 B1 | 7/2001 | Nakahata et al. | |
| 6,293,935 B1 * | 9/2001 | Kimura et al. | 604/387 |
| 6,350,711 B1 | 2/2002 | Potts et al. | |
| 6,436,081 B1 | 8/2002 | Wada et al. | |
| 6,506,185 B1 * | 1/2003 | Sauer et al. | 604/385.01 |
| 6,547,774 B2 | 4/2003 | Ono et al. | |
| 6,551,297 B2 | 4/2003 | Tanaka et al. | |
| 6,616,646 B2 | 9/2003 | Wada et al. | |
| 6,664,436 B2 | 12/2003 | Topolkaraev et al. | |
| 6,689,935 B2 | 2/2004 | Chen et al. | |
| 7,056,312 B1 | 6/2006 | Metcalf | |
| 7,067,711 B2 | 6/2006 | Kuroda et al. | |
| 7,388,123 B2 | 6/2008 | Cowell et al. | |
| 7,465,297 B2 | 12/2008 | Watanabe et al. | |
| 7,491,864 B2 | 2/2009 | Nishizawa et al. | |
| 7,530,973 B2 | 5/2009 | Tanio et al. | |
| 7,597,690 B2 | 10/2009 | Tanio et al. | |
| 7,621,899 B2 | 11/2009 | Fujikawa et al. | |
| 7,628,777 B2 | 12/2009 | Kondo et al. | |
| 7,686,790 B2 | 3/2010 | Rasmussen et al. | |
| D613,856 S | 4/2010 | Mason, Jr. | |
| 7,781,640 B2 | 8/2010 | Davis et al. | |
| 7,847,145 B2 | 12/2010 | Kurita et al. | |
| 8,030,535 B2 | 10/2011 | Hammons et al. | |
| 8,071,837 B2 | 12/2011 | Saeki et al. | |
| 8,444,618 B2 | 5/2013 | Kudo et al. | |
| 2003/0171730 A1 | 9/2003 | Kelly et al. | |
| 2005/0027278 A1 | 2/2005 | Mizutani et al. | |
| 2005/0074584 A1 | 4/2005 | Zehner et al. | |
| 2005/0124953 A1 | 6/2005 | Woltman et al. | |
| 2005/0131369 A1 | 6/2005 | Benson | |
| 2006/0271008 A1 | 11/2006 | Tanio et al. | |
| 2008/0172020 A1 | 7/2008 | Schmitz | |
| 2008/0249495 A1 | 10/2008 | Di Virgilio et al. | |
| 2009/0054860 A1 | 2/2009 | Young et al. | |
| 2009/0062764 A1 | 3/2009 | MacDonald et al. | |
| 2009/0306614 A1 | 12/2009 | Boissier | |
| 2009/0306615 A1 | 12/2009 | Olsson | |
| 2010/0152692 A1 * | 6/2010 | Ong et al. | 604/368 |
| 2012/0143163 A1 | 6/2012 | Ng | |
| 2012/0296304 A1 | 11/2012 | Choo et al. | |
| 2013/0226123 A1 | 8/2013 | Kudo et al. | |

FOREIGN PATENT DOCUMENTS

| | | |
|---|---|---|
| GB | 2 089 214 A | 6/1982 |
| JP | H06-121810 | 5/1994 |
| JP | H11-178852 | 7/1999 |
| JP | 2001-314446 | 11/2001 |
| JP | 2006-051211 | 2/2006 |
| JP | 2006-334113 | 12/2006 |
| JP | 2007-089818 | 4/2007 |
| JP | 2008-023248 | 2/2008 |
| WO | WO 9004956 | 5/1990 |
| WO | WO 97/40798 | 11/1997 |
| WO | WO 98/00082 | 1/1998 |
| WO | WO 98/51250 | 11/1998 |
| WO | WO 00/35400 | 6/2000 |
| WO | WO 01/71081 | 9/2001 |
| WO | WO 2010/070503 A2 | 6/2010 |
| WO | WO 2010/070503 A3 | 6/2010 |

OTHER PUBLICATIONS

Chinese Design Patent—CN3192181, Sep. 22, 2000, 1 page.
Abstract of Chinese Patent—CN2471314, Jan. 16, 2002, 1 page.
Abstract of Chinese Patent—CN1694665, Nov. 9, 2005, 2 pages.
Abstract of Chinese Patent—CN1917838, Feb. 21, 2007, 1 page.
Abstract of Chinese Patent—CN101090689, Dec. 19, 2007, 2 pages.
Abstract of Chinese Patent—CN101674795, Mar. 17, 2010, 1 page.
Spanish Design Patent—ESD0025203, Mar. 10, 1998, 1 page.
EU Design Patent—EU000212212-0001, Aug. 2, 2004, 1 page.
EU Design Patent—EU000824313-0001, Nov. 12, 2007, 2 pages.
EU Design Patent—EU000824313-0005, Nov. 12, 2007, 2 pages.
EU Design Patent—EU000824313-0007, Nov. 12, 2007, 2 pages.
EU Design Patent—EU000824313-0011, Nov. 12, 2007, 2 pages.
EU Design Patent—EU000824313-0012, Nov. 12, 2007; 2 pages.
EU Design Patent—EU000824313-0014, Nov. 12, 2007; 2 pages.
EU Design Patent—EU000824313-0018, Nov. 12, 2007; 2 pages.
Abstract of Japanese Patent—JP2004041339, Dec. 2, 2004, 2 pages.
Abstract of WO Patent—WO 03/065952 A1, Aug. 14, 2003, 2 pages.
Search Report and Written Opinion for PCT/CN2011/002231 dated Apr. 12, 2012, 14 pages.

* cited by examiner

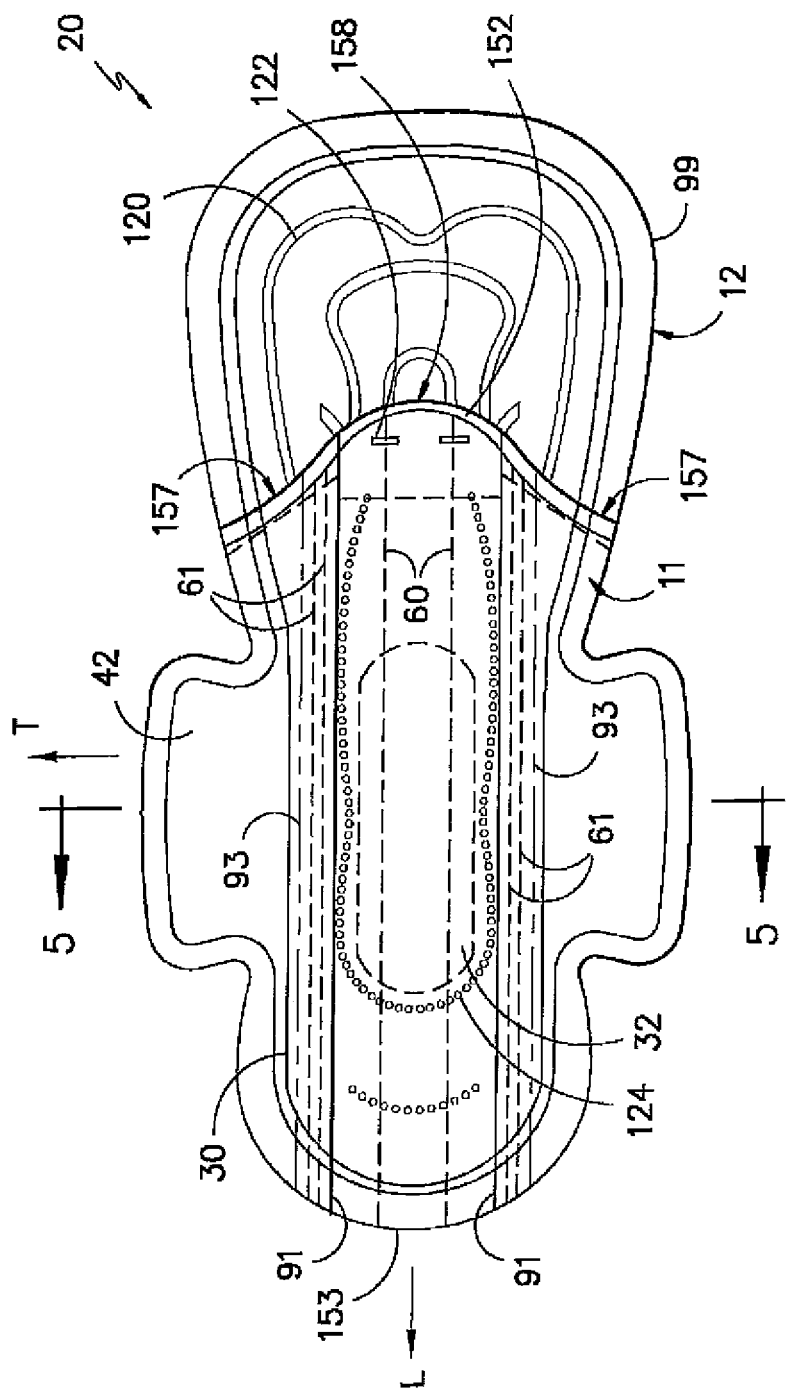
FIG. -1-

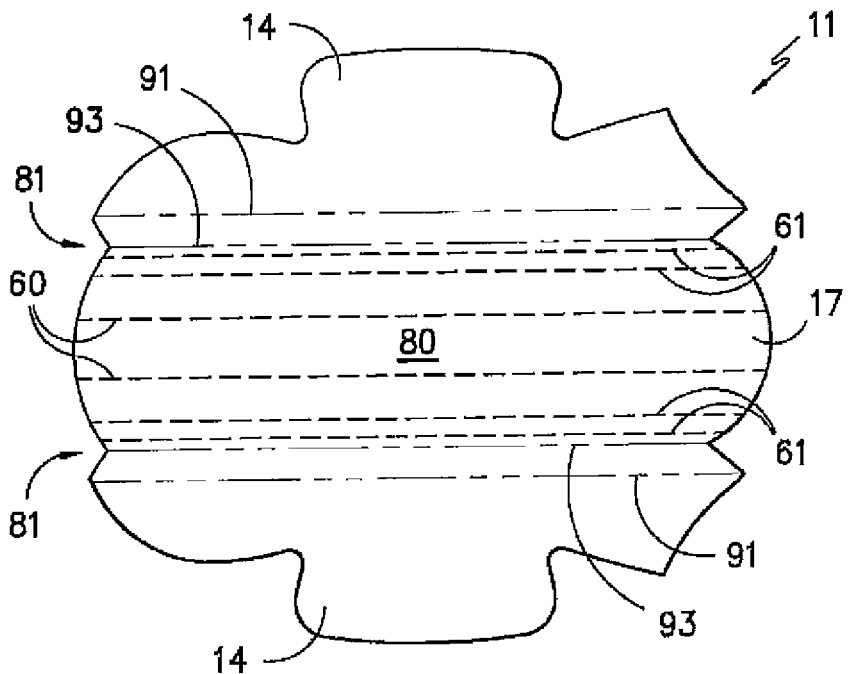
FIG. -2-
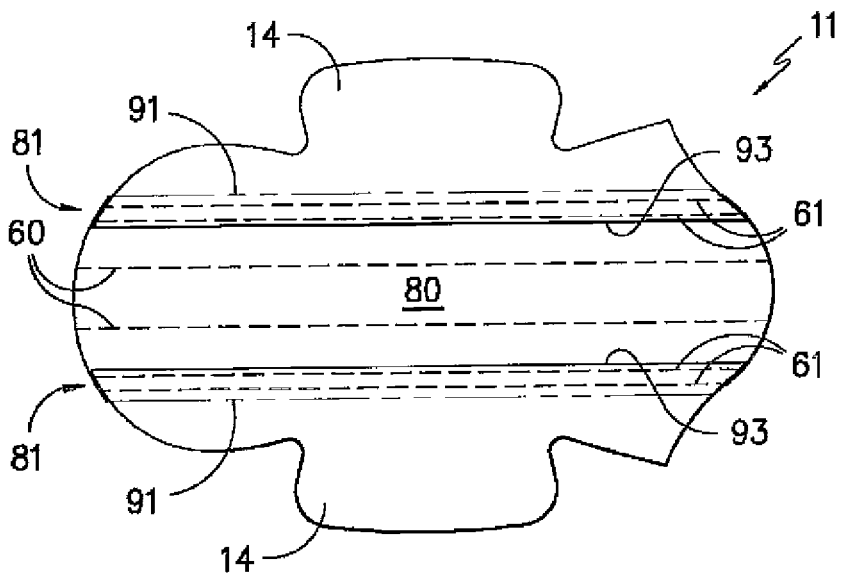
FIG. -3-

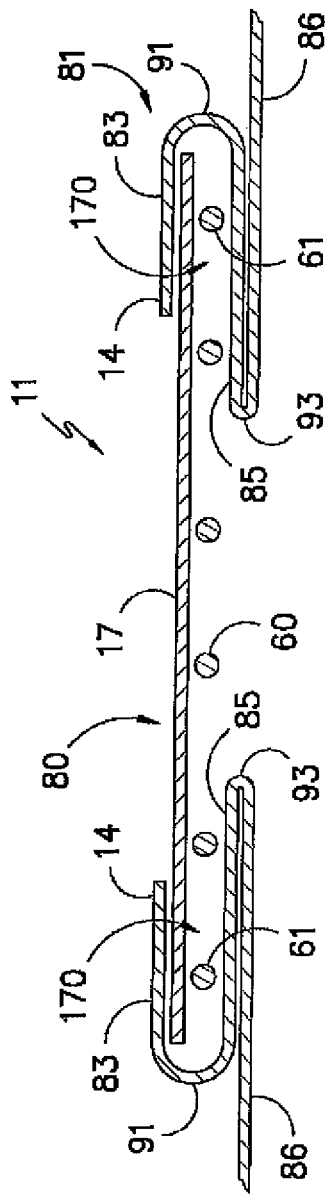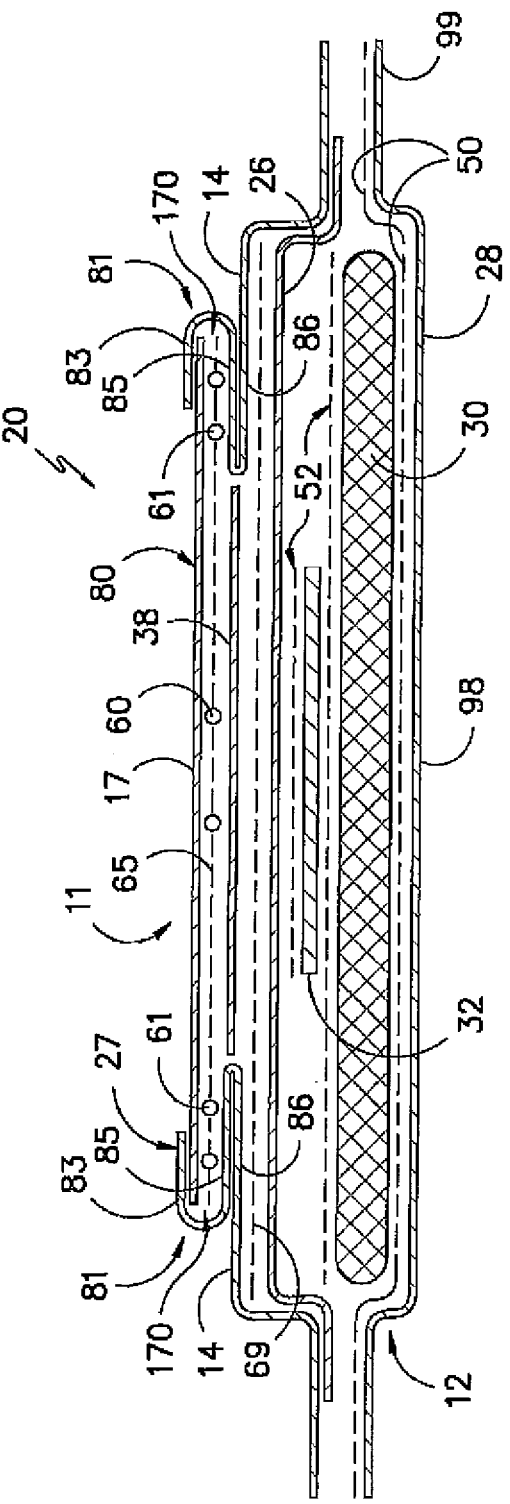

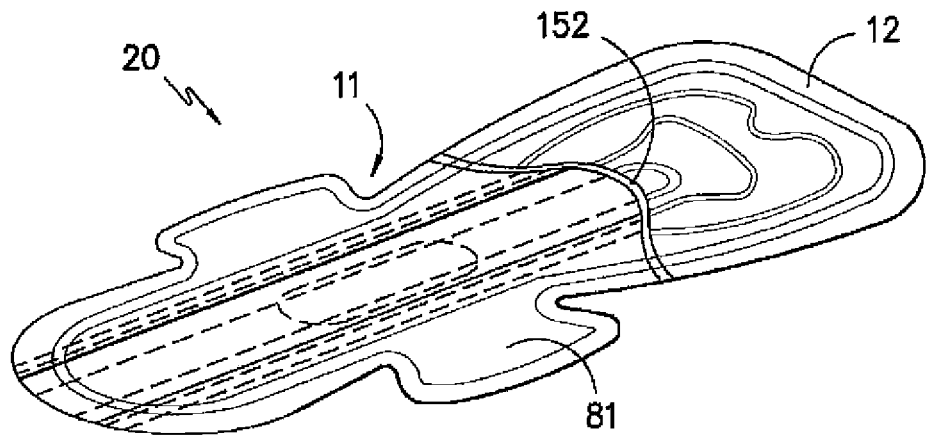
FIG. -6-
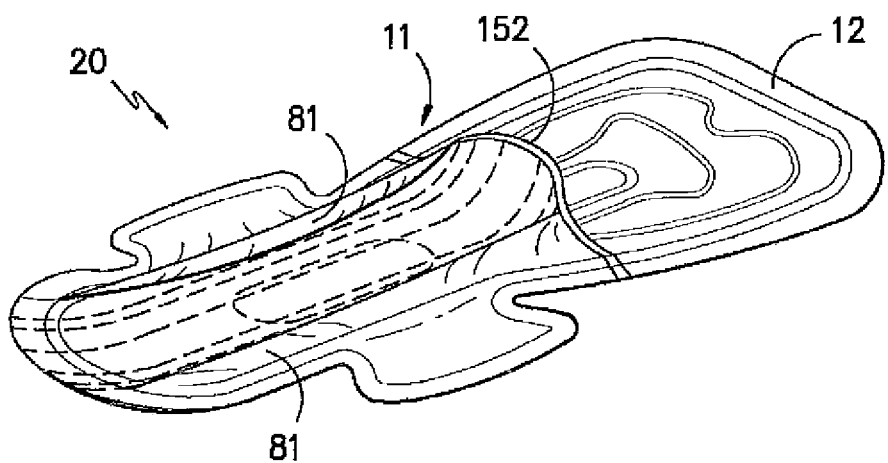
FIG. -7-

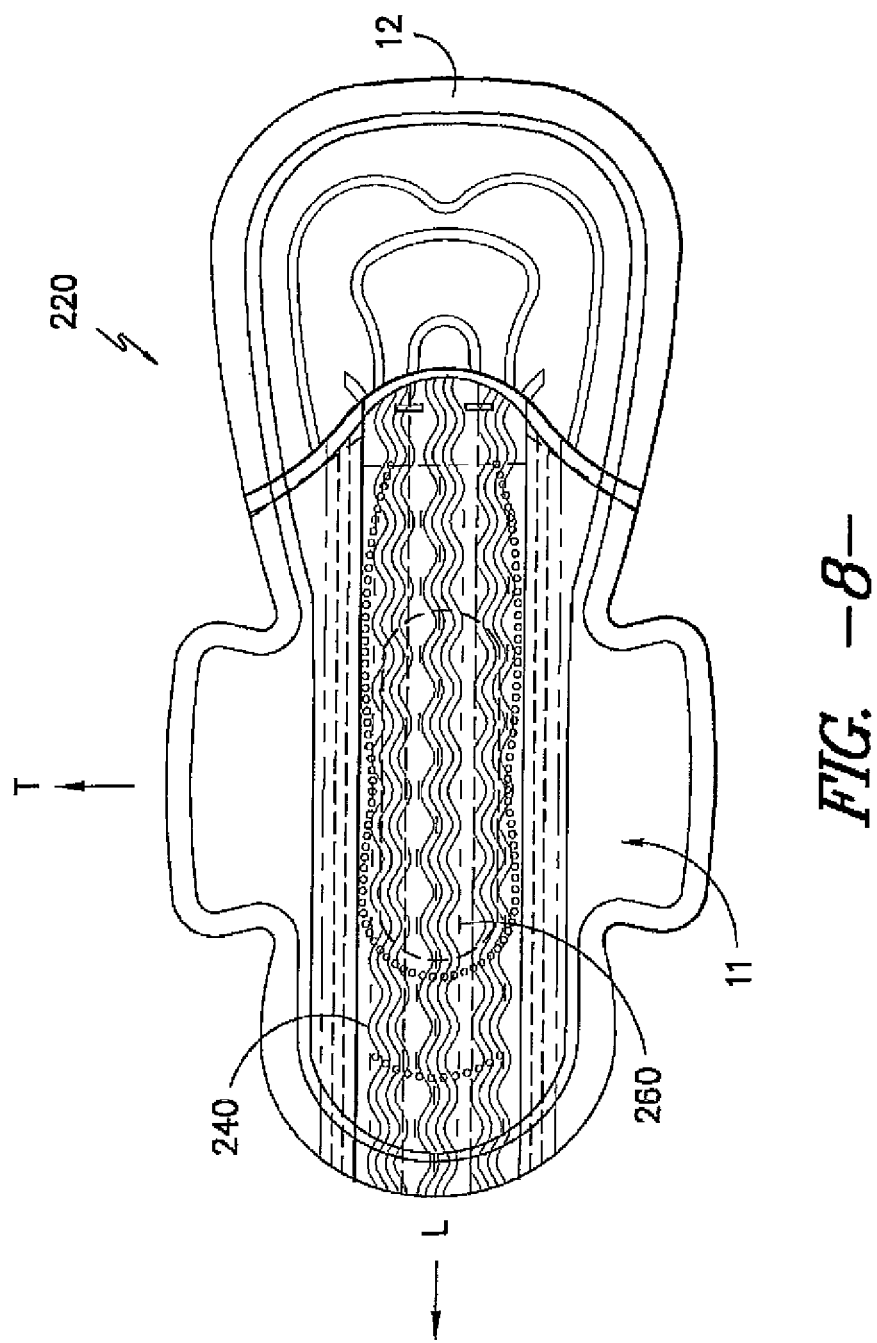
FIG. -8-

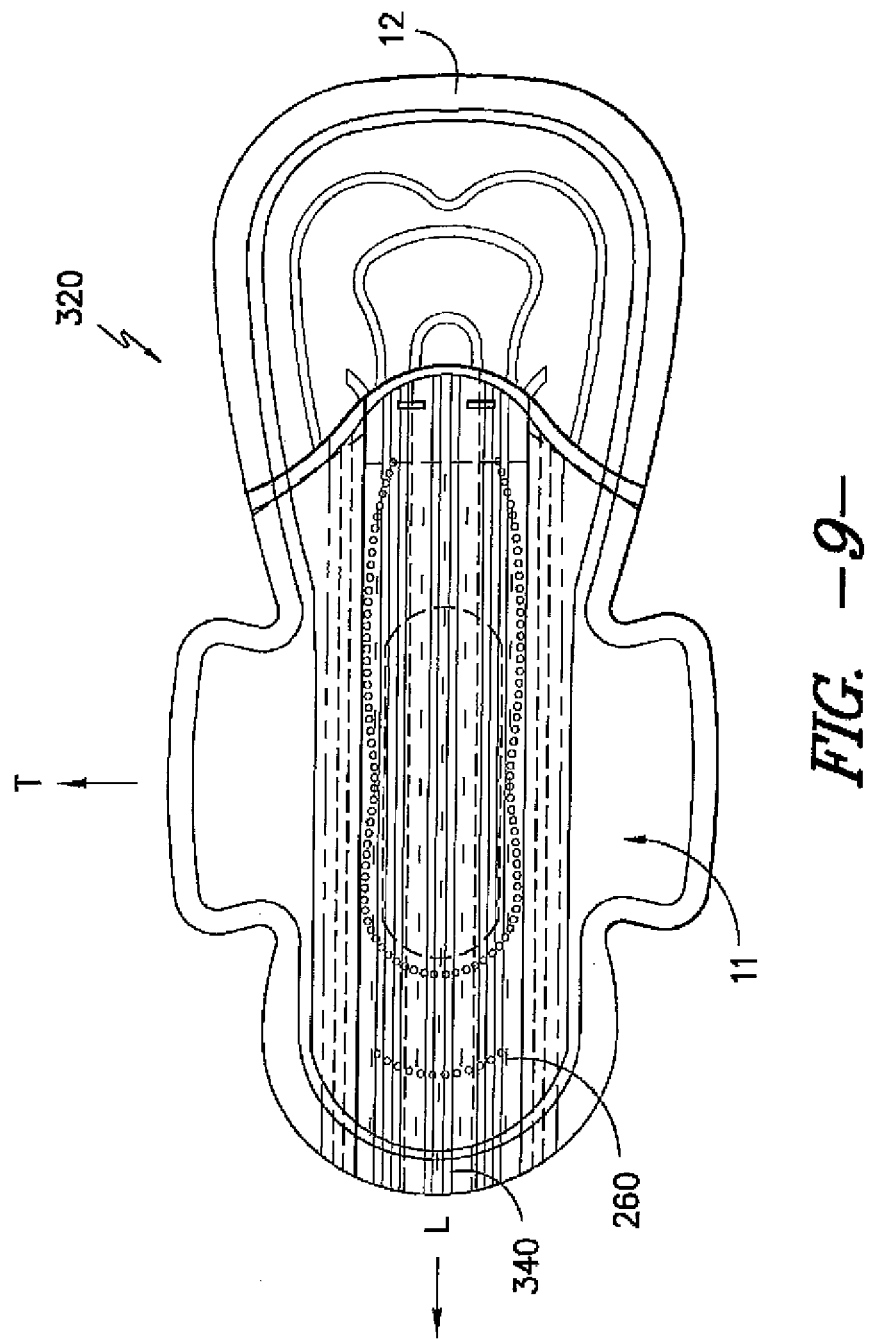
FIG. -9-

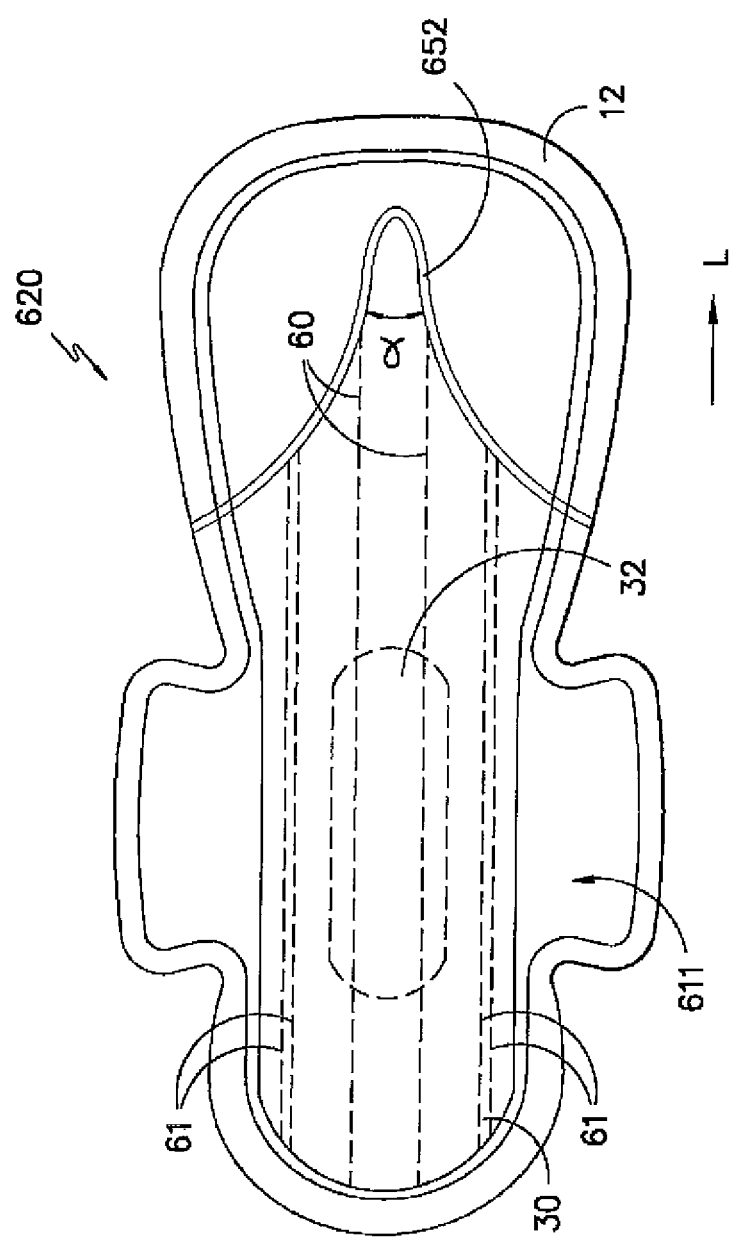
FIG. -10-

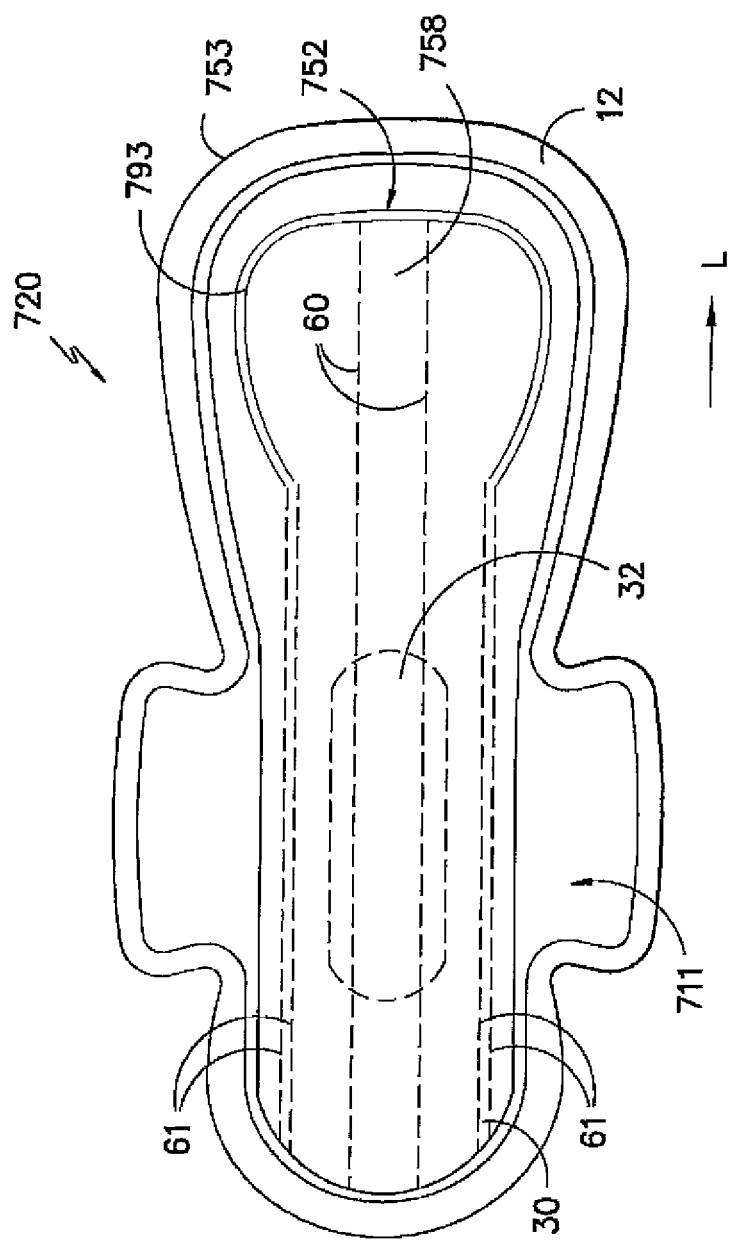
FIG. -11-

ABSORBENT ARTICLE HAVING ENHANCED LEAKAGE PROTECTION

BACKGROUND OF THE INVENTION

Absorbent articles, such as sanitary napkins, pantiliners, and incontinent pads are devices that are typically worn in the crotch region of an undergarment. Sanitary napkins and pantiliners are, for example, worn by women in a pair of panties that is normally positioned between the wearer's legs, adjacent to the perineum area. Sanitary napkins and pantiliners are designed to absorb and retain body fluids or discharges (e.g., menses) from the body of women and to prevent body and clothing from soiling. These products have developed to the extent that body exudates are quickly drawn and retained away from the wearer's skin so that the wearer remains relatively dry and comfortable. Although this improved performance enhances wearer dryness and comfort, the article can still be subject to leakage around the edges of the absorbent article, which can lead to soiling of the wearer's undergarment or clothing. This is particularly problematic in that fluid insult gushes can occur at virtually any time when the product is worn and at virtually any location (e.g., front, back, or sides of the product).

To help prevent such leakage, it is generally desirable to absorb the fluids in a central region of the article. In traditional articles, however, this is not possible as there is no barrier to bulk flow or capillary wicking from the target region (the place where intake of fluids occurs) to the edges of the pad. Thus, fluid entering the center of the pad still has the potential to travel to the edges and cause leakage. Flow from the center to the sides can be especially rapid when the article is already partially filled with fluid. In an attempt to address the problem of leakage, three-dimensional structures have been employed to enhance body fit and capture excess fluid. While these structures may add a certain level of barrier protection to the initial product, they can be easily flattened by compressional forces imparted during use. Notably, the flattening of the three-dimensional structures often occurs before the onset of a fluid insult, thereby eliminating the entire purpose of leakage control feature. Another problem with such structures is that they do not provide a consistent level of fit and fluid handling from the moment that a woman puts the article on until she removes it many hours later when it is saturated with fluid.

As such, a need exists for an absorbent article that is capable of providing better leak protection, particularly after a fluid insult.

SUMMARY OF THE INVENTION

In accordance with one embodiment of the present invention, an absorbent article is disclosed that generally extends in a plane defined by a longitudinal direction and transverse direction. The article comprises a base pad that contains a baffle and an absorbent core, and a topsheet that overlies the base pad so that the absorbent core is positioned between the topsheet and the baffle. The topsheet extends in the longitudinal direction to define a distal end and an opposing proximal end, wherein the topsheet is joined to the base pad in a manner such at least a portion of the proximal end remains generally unbonded thereto. The article also comprises a fluid-shrinkable member that extends in the longitudinal direction so that at least a portion of the fluid-shrinkable member is located adjacent to the proximal end of the topsheet.

In accordance with one embodiment of the present invention, a method for forming an absorbent article that generally extends in a plane defined by a longitudinal direction and transverse direction is disclosed. The method comprises positioning a fluid-shrinkable member adjacent to the base pad, wherein the fluid-shrinkable member extends in the longitudinal direction. The topsheet is joined to the base pad so that the fluid-shrinkable member is positioned between the topsheet and the base pad, and so that at least a portion of the proximal end of the topsheet remains generally unbonded to the base pad. At least a portion of the fluid-shrinkable member is located adjacent to the proximal end of the topsheet.

In accordance with yet another embodiment of the present invention, an absorbent article is disclosed that comprises a topsheet that defines an inner region positioned between laterally spaced first and second outer regions. The topsheet extends in the longitudinal direction to define a distal end and an opposing proximal end, wherein the topsheet is joined to the base pad in a manner such at least a portion of the proximal end remains generally unbonded thereto. An inner fluid-shrinkable member is located adjacent to the inner region of the topsheet and extends in the longitudinal direction so that at least a portion of the inner member is adjacent to the proximal end of the topsheet. An outer fluid-shrinkable member is located adjacent to the first outer region of the topsheet and extends in the longitudinal direction so that at least a portion of the outer member is adjacent to the proximal end of the topsheet.

Other features and aspects of the present invention are discussed in greater detail below.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which:

FIG. 1 is a top view of one embodiment of the absorbent article of the present invention;

FIG. 2 is a top view of one embodiment of a multi-section topsheet that may be employed in the present invention, shown in an initial unfolded configuration;

FIG. 3 shows the topsheet of FIG. 2 after being folded;

FIG. 4 is a cross-sectional view of the folded multi-section topsheet of FIG. 3;

FIG. 5 is a cross-sectional view of the absorbent article of FIG. 1;

FIG. 6 is a perspective view of the absorbent article of FIG. 1 in its initial configuration before use;

FIG. 7 is a perspective view of the absorbent article of FIG. 1 after being contacted with bodily fluids;

FIG. 8 is a top view of another embodiment of the absorbent article of the present invention;

FIG. 9 is a top view of yet another embodiment of the absorbent article of the present invention;

FIG. 10 is a top view of another embodiment of the absorbent article of the present invention; and FIG. 11 is a top view of still another embodiment of the absorbent article of the present invention.

Repeat use of reference characters in the present specification and drawings is intended to represent the same or analogous features or elements of the invention.

DETAILED DESCRIPTION OF REPRESENTATIVE EMBODIMENTS

Definitions

As used herein, the term "body-facing surface" generally refers to an outwardly facing surface of an absorbent article that is intended to be disposed toward or placed adjacent to the body of a wearer during ordinary use. This surface may be defined by a topsheet, which also includes an opposing inwardly facing surface.

As used herein, the term "garment-facing surface" generally refers to an outwardly facing surface of an absorbent article that is intended to be disposed away from the body of a wearer during ordinary use. The surface is typically placed adjacent to the wearer's undergarments when the article is worn. This surface may be defined by a baffle, which also includes an opposing inwardly facing surface.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to an absorbent article that is capable of inhibiting leakage of a fluid insult. The absorbent article may particularly be a feminine care article, such as a sanitary napkin, pad, tampon, etc. The absorbent article contains a fluid-shrinkable member, topsheet, and a base pad that includes a baffle and an absorbent core positioned between the topsheet and the baffle. The fluid-shrinkable member extends in a longitudinal direction of the article so that at least a portion of the member is located adjacent to an end of the topsheet. At least a portion of the end of the topsheet remains generally unbonded to the base pad. Thus, when the fluid-shrinkable member contracts upon contacting a fluid insult, the end of the topsheet can rise outwardly from the plane of the absorbent article. The raised area creates a barrier to the leakage of fluids from the center of the article towards its end. In certain embodiments, contraction of the fluid-shrinkable member can also cause an outer region of the topsheet to rise outwardly from the plane of the absorbent article to create a barrier to the leakage of fluids from the center of the article towards the side edge. Notably, because such barriers are generally created only after contact with a fluid insult, their effectiveness is not diminished through use of the article prior to the insult.

Referring to FIGS. 1 and 5, one particular embodiment of a feminine care absorbent article 20 of the present invention will now be described in more detail. As shown, the feminine care absorbent article 20 includes a topsheet 11 that generally overlies a base pad 12. The configuration and materials used to form the base pad 12 are not generally critical, so long as it is capable of absorbing bodily fluids. In the illustrated embodiment, for example, the base pad 12 includes a liquid-permeable cover 26, a generally liquid-impermeable baffle 28, and an absorbent core 30 positioned therebetween. The cover 26 can be constructed of any woven or nonwoven material that is easily penetrated by bodily exudates. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable cover material is a bonded carded web made of polypropylene and polyethylene such as that used as topsheet stock for KOTEX® pantiliners and obtainable from Sandler AG (Germany). U.S. Pat. No. 4,801,494 to Datta, et al. and U.S. Pat. No. 4,908,026 to Sukiennik, et al. teach various other topsheet materials that may be used in the present invention. The cover typically has a basis weight of less than about 100 grams per square meter (gsm), and in some embodiments, from about 10 gsm to about 40 gsm.

The baffle 28 is generally liquid-impermeable and defines a garment-facing surface 98 of the article 20. The baffle 28 may permit a passage of air or vapor out of the absorbent article 20, while still blocking the passage of liquids. Any liquid-impermeable material may generally be utilized to form the baffle 28. For example, one suitable material that may be utilized is a microporous polymeric film, such as polyethylene or polypropylene. In particular embodiments, a polyethylene film is utilized that has a thickness in the range of about 0.2 mils to about 5.0 mils, and particularly between about 0.5 to about 3.0 mils. A specific example of a baffle material is a polyethylene film such as that used in KOTEX® pantiliners and obtainable from Pliant Corporation, Schaumburg, Ill., USA.

As indicated above, an absorbent core 30 is positioned between the cover 26 and the baffle 28 that provides capacity to absorb and retain bodily exudates. The absorbent core 30 may be formed from a variety of different materials and contain any number of desired layers. For example, the core 30 typically includes one or more layers (e.g., two layers) of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

Although not required, the base pad 12 may also contain other additional layers as is known in the art. In FIGS. 1 and 5, for example, a liquid-permeable intake layer 32 is positioned between the cover 26 and the absorbent core 30. The intake layer 32 may be made of a material that is capable of rapidly transferring, in the z-direction, body fluid that is delivered to the cover 26. The intake layer 32 may generally have any shape and/or size desired. In one embodiment, the intake layer 32 has a generally ovular shape, with a length and/or width less than the overall length and/or width of the base pad 12. Any of a variety of different materials are capable of being used for the intake layer 32 to accomplish the above-mentioned functions. The material may be synthetic, cellulosic, or a combination of synthetic and cellulosic materials. For example, airlaid cellulosic tissues may be suitable for use in the intake layer 32. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The cover 26 may be maintained in secured relation with the absorbent core 30 by bonding all or a portion of the adjacent surfaces to one another. A variety of bonding mechanisms known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent (e.g., ultrasonically fusing). In the embodiment shown in FIG. 5, for instance, the cover 26 is bonded to the baffle 28 with an adhesive 50, which can optionally extend along a substantial length of the pad 12. If desired, the adhesive 50 may also be extended to the center of the baffle 28 so that it bonds together the baffle 28 and the absorbent core 30. Adhesives 52 may also be employed to bond the cover 26 to the intake layer 32 and the intake layer 32 to the absorbent core 30 if desired.

The topsheet 11 helps provide comfort and conformability, and also helps direct bodily exudates away from the body toward the absorbent core 30. The topsheet 11 generally extends over the upper, bodyside surface of the base pad 12, but can alternatively extend around the article to partially or entirely, surround or enclose the base pad. Typically, the topsheet 11 and the baffle 28 of the base pad 12 have peripheral margins 99 that extend outwardly beyond the terminal, peripheral edges of the absorbent core 30, and the extending margins are joined together to partially or entirely, surround or enclose the absorbent core. The topsheet 11 contacts the body of the user and is liquid-permeable. The topsheet 11 may be formed from one or multiple layers of materials. The liquid-permeable topsheet 11 has an outwardly facing surface 27 that may contact the body of the wearer and receive fluids from the body.

Generally speaking, the topsheet 11 defines an inner region 80 positioned between laterally spaced first and second outer regions 81. The inner and outer regions may be formed from a single section of material, or from multiple sections. In FIGS. 1 and 5, for instance, the topsheet 11 is formed from a center section 17 that is positioned between side sections 14. Such multi-section topsheet configurations are known in the art and described in more detail, for instance, in U.S. Pat. No. 5,415,640 to Kirby, et al., which is incorporated herein in its entirety by reference thereto for all purposes. Whether having one or multiple sections, the topsheet 11 may be made from any liquid-permeable material known in the art. Examples of such materials are described above with respect to the cover 26, although the cover 26 and the topsheet 11 need not be formed from the same materials. In one particular embodiment, for example, the center section 17 and/or the side sections 14 are both formed from a bonded carded web made of polypropylene and polyethylene, such as that used as topsheet stock for KOTEX® pantiliners and obtainable from Sandler Corporation (Germany). Such materials typically have a basis weight of less than about 100 gsm, and in some embodiments, from about 10 gsm to about 40 gsm.

The topsheet 11 also typically has a distal end 153 and an opposing proximal end 152. Although the proximal and distal ends are shown herein as the front and rear ends of the article, respectively, the terms "proximal" and "distal" do not necessarily refer to the rear and front ends of the topsheet as such terms are employed only for the sake of convenience. In one embodiment, for example, the term "proximal" may refer to the front end of the topsheet. In any event, the shape of the proximal and/or distal ends of the topsheet may be configured to help improve the comfort of the article during use. In the embodiment shown in FIG. 1, for example, the proximal end 152 of the topsheet 11 may have a configuration in which peripheral portions 157 taper outwardly from a central portion 158. This forms a general parabolic shape that can better conform to the body, both before and after fluid insult. Depending on the desired fit, the angle of the taper may generally range from about 10° to about 180°, and in some embodiments, from about 40° to about 80°. In FIG. 10, for instance, one embodiment of an absorbent article 620 is shown that contains a topsheet 611 having a proximal end 652 with a relatively small taper angle "α."

A fluid-shrinkable member is also employed in the absorbent article of the present invention that can shrink and pull a portion of the absorbent article inwardly (i.e., toward the longitudinal and/or transverse center of the article) upon fluid insult. Any number of fluid-shrinkable members may generally be employed, such as from 1 to 20, in some embodiments from 2 to 15, and in some embodiments from 4 to 10. In the illustrated embodiment, for example, six (6) separate fluid-shrinkable members are employed. The fluid-shrinkable members can be in the form of yarn, fiber, filament, tape, film, nonwoven, laminate, etc. Such materials are described in more detail in U.S. Patent Application Publication No. 2010/0152692 to Ong, et al., which is incorporated herein in its entirety by reference thereto for all relevant purposes. In desirable aspects, the fluid-shrinkable members have a high ratio of length to width (e.g., diameter) so that they are in the form of a string. For example, the aspect ratio may be about 10 or more, in some embodiments about 40 or more, and in some embodiments, about 100 or more.

Regardless of their form, the fluid-shrinkable members may demonstrate shrinkage ability in water, urine, menstrual fluid, etc. Shrinkage of at least about 10%, such as at least about 20%, or at least about 40%, or from about 40% to about 60% or more by length is suitable. Suitable materials for the fluid-shrinkable member include modified polyvinyl alcohol (PVA), modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and crosslinked fiber thereof; wool or silk modified in the same manner as described above; modified synthetic fiber, such as a partially saponified acrylonitrile series of fiber and vinilon fiber which is partially esterified by maleic acid, carboxymethylcellulose and hydrolyzed acrylic fiber. In one particular aspect, a suitable modified PVA fluid-shrinkable member can be obtained from Kuraray Group, Japan.

If desired, the fluid-shrinkable members can include an optional amount of superabsorbent materials. Examples of suitable superabsorbent materials include poly(acrylic acid) and poly(methacrylic acid), poly(acrylamides), poly(vinyl ethers), maleic anhydride copolymers with vinyl ethers and α-olefins, poly(vinyl pyrrolidone), poly(vinylmorpholinone), poly(vinyl alcohol), and salts and copolymers thereof. Other superabsorbent materials include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum, and so forth. Mixtures of natural and wholly or partially synthetic superabsorbent polymers may also be useful in the present invention. The superabsorbent material can be present in the fluid-shrinkable member in an amount as desired, provided that it does not diminish the effectiveness of the shrinkable member. For example, in some aspects, the fluid-shrinkable members can contain up to about 1 wt. %, such as up to about 5 wt. %, or even up to about 10 wt. % or more superabsorbent material to provide improved benefits.

The fluid-shrinkable members can also include an optional elastomeric polymer having a permeability for water vapor to facilitate moisture absorption. The elastomeric polymer component may be present in an amount effective to achieve the desired dimensional change properties. The elastomeric polymer can be present in an amount as desired, provided that it does not diminish the effectiveness of the shrinkable member. For example, in some aspects, the fluid-shrinkable members can contain up to about 1 wt. %, such as up to about 5 wt. %, or even up to about 10 wt. % or more elastomeric polymer to provide improved benefits. Examples of suitable elastomeric polymers include, but are not limited to, thermoplastic polyurethanes, poly(ether-amide) block copolymers, polyolefins (e.g., polyethylene, polypropylene, etc.), styrene-butadiene copolymers, silicon rubbers, synthetic rubbers such as nitrile rubber, styrene isoprene copolymers, styrene ethylene butylene copolymers, butyl rubber, nylon copolymers, spandex fibers comprising segmented polyurethane, ethylene-vinyl acetate copolymer or mixtures thereof.

The fluid-shrinkable members are incorporated into the absorbent article in a selectively controlled manner to optimize the ability to reduce leakage. For example, at least one fluid-shrinkable member is employed that generally extends in a longitudinal direction of the article and is disposed adjacent to an end of the topsheet. The placement of a fluid-shrinkable member "adjacent" to an end does not necessarily mean that the member must be directly adjacent to or terminate at the end of the topsheet. In fact, the member may terminate before and/or after reaching the end of the topsheet, so long as its contraction helps facilitate the creation of a barrier in accordance with the present invention. For example, in certain embodiments, a fluid-shrinkable member may terminate a distance of about 10 millimeters or less, in some embodiments about 5 millimeters or less, and in some embodiments, about 2 millimeters or less away from an end of the topsheet.

Referring again to FIGS. 1 and 5, for example, a plurality of outer, fluid-shrinkable members 61 and inner, fluid-shrinkable members 60 are employed that extend in a longitudinal direction "L" and are located adjacent to the proximal end 152. The outer members 61 are also disposed adjacent to outer regions 81 of the topsheet 11, and the inner members 60 are spaced laterally inward from the outer members 61 so that they are located adjacent to the inner region 80 of the topsheet 11. By disposing fluid-shrinkable members in this manner, the end(s) and the side(s) of the topsheet are capable of rising outwardly from the plane of the absorbent article during use to create a cup-shaped barrier to the leakage of fluids from the center of the article towards the edges. The relative distance that the side(s) and/or end(s) of the topsheet are capable of being raised may vary, but is typically at least about 1 millimeter, in some embodiments at least about 4 millimeters, and in some embodiments, from about 10 to about 70 millimeters above the original plane of the article. Likewise, the angle of orientation of the side(s) and/or end(s) upon rising may range from about 1° to about 90°.

In the embodiment illustrated, at least a portion of the proximal end 152 remains generally unbonded to the base pad 12 (e.g., baffle 28) so that it is capable of forming a raised area upon contraction of the fluid-shrinkable members. Although not shown, a portion of the distal end 153 may also be generally unbonded to the base pad 12 (e.g., baffle 28) so it can form a raised barrier upon the contraction a fluid-shrinkable member located proximate thereto. It should be understood that while such ends may be generally unbonded, some portion of the end can nevertheless still be joined to the base pad. In one embodiment, for example, peripheral portions 157 of the proximal end 152 may be joined to the base pad 12, while a central portion 158 remains generally unbonded. In this configuration, the central portion 158 of the proximal end 152 can raise outwardly from the plane of the absorbent article during use to create an additional barrier to the leakage of fluids from the center toward the end of the article.

Any of a variety of different bonding patterns and configurations may be employed to achieve the desired attachment of the proximal end of the topsheet to the base pad. For example, in one embodiment, a length that spans a distance of from about 20 to about 200 millimeters, and in some embodiments, from about 20 to about 40 millimeters from the tapered peak of the proximal end 152 to a horizontal line may remain unbonded to the base pad 12. The other areas of the topsheet 11 may be bonded to the base pad 12 using any pattern desired, such as continuous or discontinuous (e.g., toothed, stepped, dots, etc.). Any known bonding method may be employed, such as adhesive bonding, ultrasonic bonding, mechanical bonding, heat bonding, etc.

Turning now to FIGS. 6-7, the ability of the fluid-shrinkable members to form a barrier to leakage during use will be described in more detail. Prior to contact with bodily fluids, the topsheet 11 remains substantially flat as shown in FIG. 6. However, upon a gush of fluid, the contraction of the fluid-shrinkable members 60 and/or 61 pulls the proximal end 152 upwardly and in a longitudinal direction toward the center of the absorbent article 20. This creates a barrier to the leakage of fluids from the center toward the rear of the article. Contraction of the fluid-shrinkable members 61 also causes the outer regions 81 of the topsheet 11 to rise (e.g., buckle) and create a barrier to the leakage of fluids from the center toward the sides of the article. Because these barriers are created only after contact with a fluid insult, their effectiveness is not generally diminished through use of the article prior to the insult.

To facilitate the ability of the proximal end 152 of the topsheet 11 to rise up in the manner described above, the length of the topsheet 11 may be less than that of the baffle 28. For example, the ratio of the length of the topsheet 11 to the length of the baffle 28 (in the longitudinal direction) may be from about 0.2 to about 1.0, in some embodiments from about 0.3 to about 0.9, and in some embodiments, from about 0.5 to about 0.8. Nevertheless, it should be understood that the topsheet 11 may also have a length that is the same or even greater than that of the baffle 28, such as a length ratio of from about 1.0 to about 10.0. In such embodiments, it is often desired to form the proximal end and/or distal end through a cut made in the topsheet material. Referring to FIG. 11, for example, one embodiment of an absorbent article 720 is shown that contains a topsheet 711. In this particular embodiment, the topsheet 711 extends in the longitudinal direction "L" to a first end 753 that is joined to the baffle and defines a length that is substantially the same as the base pad 12. Nevertheless, the first end 753 is not the proximate and/or distal end as defined herein. More particularly, a portion 758 of the topsheet 711 is formed to define a second end 752 located adjacent to the fluid-shrinkable members 60. The portion 758 is generally unbonded to the base pad 712 and is thus capable of rising up during use due to the constriction of the fluid-shrinkable members 60 during use. Thus, in this particular embodiment, the second end 752 is considered the "proximal" end. Any technique may generally be employed to form the second end 752, such as by cutting, slitting, etc. the topsheet 511 along a line 793, or by simply attaching a separate material thereto.

A variety of different techniques may be employed to incorporate the fluid-shrinkable members into the absorbent article. In one embodiment, for example, the fluid-shrinkable members may simply be attached to a garment-facing surface of the topsheet. In FIGS. 1 and 5, for example, the fluid-shrinkable members are directly connected to the topsheet 11 with an adhesive 65. Other suitable bonding techniques may also be employed, such as stitching, thermal bonds, ultrasonic bonds, embossing, crimping, entangling, fusing, etc., and combinations thereof. It should also be understood that such members may be indirectly connected to the topsheet, such as by using one or more layers that are disposed between the members and the topsheet and attached thereto. Bonding may occur over the entire length of each member. In other embodiments, however, only a portion of a member may be bonded, such as through the use of one or more spot welds. In some aspects, it is desirable to anchor the ends of the member into the article while keeping the central length of the member free from bonds to provide improved shrinkage performance.

If desired, additional techniques may be employed to help further ensure that the fluid-shrinkable members are retained in the absorbent article during use, and also to further bolster the three-dimensional topography that can be achieved by the present invention. For example, in certain embodiments, the topsheet may be folded to create a pocket within which the outer members can reside. The pocket helps secure the fluid-shrinkable members and also adds bulk to the topsheet. In FIGS. 1 and 5, for instance, the outer regions 81 of the topsheet 11 are folded to create a pocket 170 within which the fluid-shrinkable members 61 are retained.

FIGS. 2-4 illustrate in more detail the manner in which the topsheet 11 can be folded to achieve the desired pocket configuration. More specifically, FIG. 2 shows the topsheet 11 in its initial unfolded configuration. To create the desired pocket, the outer regions 81 are bent inwardly along fold lines 91 so that a first portion 83 of the topsheet 11 is disposed above a second portion 85 (FIGS. 3 and 4). In this manner, the fluid-shrinkable members 61 can be sandwiched in the pocket 170 formed between the first portion 83 and second portion 85 (FIG. 4). The outer regions 81 may also be bent outwardly along fold lines 93 to create a z-shaped folded configuration in which a third portion 86 of the topsheet 11 extends generally parallel to the base pad 12. If desired, the outer members 61 may also be disposed within the pocket formed between the second portion 85 and the third portion 86. It should be noted that the referenced portions 83, 85, and 86 may be formed by one or multiple sections of the topsheet 11 as discussed above. For example, in the illustrated embodiment, each of the portions 83, 85, and 86 are formed by the side sections 14 of the topsheet 11. In alternative embodiments, however, the center section 17 may constitute the first portion, second portion, and/or third portion, and may optionally be folded to achieve the desired pocket configuration.

In certain embodiments, the manner in which the pocket 170 is formed can help facilitate the ability of the outer regions 81 to rise upwardly. For example, in one embodiment, the first portion 83 of the side section 14 can be wrapped around the center section 17 and remain generally unbonded thereto. In this manner, contraction of the members 61 forces upward the center section 17, which in turn forces upward the first portion 83. Unlike the center section 17, however, the first portion 83 is able to rise up without restriction because it is generally unbonded. It should be understood, however, that the first portion 73 can also be bonded to the center section if so desired.

In addition to the longitudinally extending fluid-shrinkable members described above, fluid-shrinkable members may also be disposed at other locations within the absorbent article and in various different configurations. In certain embodiments, for example, fluid-shrinkable members may be employed that extend in the transverse direction to form a cross-stitching pattern with longitudinally-extending members. Various other patterns that may be formed by the fluid-shrinkable members may include, for instance, diagonal patterns, wavy patterns, circular patterns, triangular patterns, etc. In addition, while the aforementioned embodiments have exemplified fluid-shrinkable members in a generally planar configuration, it should be understood that the fluid-shrinkable members can also be present at any angle from plane of the absorbent article, such as substantially perpendicular to the plane of the article (e.g., into the absorbent core).

If desired, additional materials may also be employed in the absorbent article. Referring again to FIGS. 1 and 5, for instance, a fluid distribution layer 38 is disposed between the topsheet 11 and the base pad 12. Among other things, the fluid distribution layer 38 may add bulk to the article, which can improve the consistency of the fit and fluid handling capacity both before and after the fluid insult, as well as aid in securing the interior fluid-shrinkable members to the topsheet 11. For example, the adhesive 65 may connect the fluid-shrinkable members 60 to the center section 17 of the topsheet 11 and to the fluid distribution layer 38. The fluid distribution layer 38 may be formed from a material that is substantially hydrophobic, such as a nonwoven web composed of polypropylene, polyethylene, polyester, etc. One example of such a material is a spunbond web composed of polypropylene, bicomponent fibers, which may be round, tri-lobal or poly-lobal in cross-sectional shape and which may be hollow or solid in structure. Typically the webs are bonded, such as by thermal bonding, over about 3% to about 30% of the web area. Such materials typically have a basis weight of less than about 100 gsm, and in some embodiments, from about 10 gsm to about 40 gsm. Other examples of suitable materials that may be used for fluid distribution layer 38 are described in U.S. Pat. No. 4,798,603 to Meyer, et al. and U.S. Pat. No. 5,248,309 to Serbiak, et al. To adjust performance, the fluid distribution layer may also be treated with a selected amount of surfactant to increase its initial wettability.

The absorbent article 20 may also include laterally extending wing portions 42 that may be integrally connected to side regions along the intermediate portion of the article. For example, the wing portions 42 may be separately provided members that are subsequently attached or otherwise operatively joined to the intermediate portion of the article. In other configurations, the wing portions may be unitarily formed with one or more components of the article. As representatively shown in FIG. 1, for example, either or both wing portions 42 may be formed from a corresponding, operative extension of the material employed to form the topsheet 11. Alternatively, either or both wing portions 42 may be formed from a corresponding, operative extension of the material employed to form the baffle, or formed from a corresponding, operative combination of the topsheet and baffle materials.

If desired, various other features may also be incorporated into the absorbent article to help reduce the likelihood of leakage upon a fluid insult. In one embodiment, for example, embossed regions may be formed in one or more layers of the article to serve a variety of different purposes. In the embodiment shown in FIGS. 1-7, for example, embossed regions 120 and 124 may be formed in the base pad 12 to help guide fluid in the desired manner and create additional bulk in the article. The embossed regions 120 are formed in the absorbent core 30 and the embossed regions 124 are formed in the cover 26. In yet other embodiments, embossed regions may be formed on the topsheet 11. For example, embossed regions 122 may be formed which, in addition to serving as a fluidic guide, may also help retain the fluid-shrinkable members 60 in the desired position during use. Additional embossed regions may also be employed in the topsheet to create a three-dimensional surface topography that can increase available surface area and further improve the ability of the article to take in bodily fluids and inhibit leakage. The embossed regions may also improve the consistency of the fit and fluid handling properties of the article, both before and after a fluid insult.

Referring to FIG. 8, for example, one particular embodiment of an absorbent article 220 is shown that contains embossed regions 240 on a body-facing surface of the topsheet 11. Any number of embossed regions may be employed in the present invention, such as 1 or more, in some embodiments 2 or more, in some embodiments from 3 to 20, and in some embodiments, from 5 to 15 individually spaced apart embossed regions. The embossed regions 240 are defined by densified edges that extend in a wave pattern of alternating crests and troughs along the longitudinal direction "L." For sake of convenience, the term "crests" refers to peaks facing toward the right side of the topsheet shown in FIG. 8, and the "troughs" refers to peaks facing the left side. Although a sinusoidal wave pattern is depicted, it should be understood that other known wave patterns may be employed, such as sawtooth waves, square waves, triangle waves, etc. The pattern of the embossed regions 240 may be a regular periodic wave in that the wavelength (e.g., distance between contiguous crests and/or contiguous troughs) and amplitude (e.g., difference in height between a crest and trough) remain substantially constant as shown in FIG. 8. In certain embodiments, however, the pattern may also be an irregular wave in that the wavelength and/or amplitude may vary at different points of the wave. The wave pattern of the embossed regions 240 may also be continuous (e.g., without interruption), as shown in FIG. 8, or discontinuous in nature. A discontinuous pattern may be for example made of dots, broken lines or other interrupted elements. The number of elements per unit length does not need to be constant but may vary along the length of the pattern or across the different discontinuous patterns when more than one are present. Although not necessarily required, it is often desired that the pattern, whether continuous or discontinuous, extends along substantially the entire length of the cover 26.

In FIG. 8, the embossed regions 240 are provided with a wave pattern, but this is by no means a requirement. In certain embodiments, for example, one or more of the embossed regions may also be arranged in a pattern that is not wavelike in nature. Referring to FIG. 9, for example, one embodiment of an absorbent article 320 is shown that contains embossed regions 340 that are arranged substantially parallel to the longitudinal direction "L." Of course, any of a variety of other embossing patterns may also be employed in the present invention, such as dots, squares, rectangles, etc. Regardless of their form, it is typically desired that the embossed regions are arranged in a generally symmetrical manner about a longitudinal centerline and/or transverse centerline of the topsheet 11. Also, although not required, the embossed regions may be arranged in sets (e.g., pairs) to further enhance aesthetic appeal.

If desired, a plurality of apertures may also be formed in the topsheet. When employed in conjunction with embossed regions, the apertures may be arranged proximate or adjacent to such embossed regions. In FIG. 8, for example, apertures 260 are shown arranged proximate to contiguous crests and/or contiguous troughs of at least one of the embossed regions 240. In this context, the term "proximate" generally means that an aperture is located on the same side of the longitudinal axis of the wave as the crest or trough, and at least a portion of the aperture is also located within a wavelength boundary defined by the crest or trough. The apertures may extend in substantially the same direction as the embossed region to which they are proximately located. For example, the apertures 260 of FIGS. 8 and 9 are arranged in columns that generally extend in the same longitudinal direction "L" as the embossed regions. If desired, the apertures may be positioned in a column that is tangent to an embossed region.

The apertures may possess any desired shape or size, such as circular, elliptical, triangular, rectangular, square, slits, etc. Although not required, it is often desired that the apertures are elongated. In the embodiments shown in FIGS. 8-9, for example, the apertures 260 are in the form of elongated slits having a large aspect ratio (length divided by width), such as about 5 or more, in some embodiments about 10 or more, and in some embodiments, from about 20 to about 1000. One benefit of such elongated slits is that they can provide a unique aesthetic appeal. Nevertheless, during use of the absorbent article, the handling of the article and movement of the wearer may cause the topsheet to bend and stretch, thereby resulting in the expansion of the slits into larger apertures. The apertures 260 possess a major axis oriented in the longitudinal direction "L" of the article and a minor axis in the transverse direction "T." In this manner, the apertures themselves extend in the same longitudinal direction "L" as the embossed regions and are optionally positioned tangent to the crests and/or troughs of an embossed wave pattern (FIG. 8). This particular geometric configuration can enhance both the aesthetic appeal and absorbent properties of the article. Nevertheless, it should be understood that the apertures need not be oriented in this particular fashion.

The embossed regions and/or apertures described above may be formed using any known conventional techniques known in the art. Suitable techniques include, for instance, the use of raised elements to impart the desired pattern or apertures. Thermal and/or ultrasonic bonding techniques may be employed for this purpose. For instance, a suitable process may involve thermal bonding wherein a layer is passed through two rolls (e.g., steel, rubber, etc.) in which one is engraved with an embossing and/or aperture pattern and the other is flat. One or both of the rolls may be heated. The embossed regions and apertures may be formed simultaneously or separately. In one embodiment, for example, the topsheet is initially formed with the desired apertures and then embossed.

If desired, additional structural members may also be employed to further enhance the three-dimensional topography of the absorbent article. Fluidic guides may also be employed in the present invention to assist in leakage prevention. For instance, U.S. Pat. No. 5,614,295 to Quincy, III, et al., which is incorporated herein in its entirety by reference thereto, describes a fibrous web that is specifically configured to distribute liquid in the direction of the orientation of the fibers. The web is formed from a first zone of fibers treated with a surfactant and a second zone of fibers exposed to a corona field. U.S. Pat. No. 7,388,123 to Cowell, et al., which is incorporated by reference, describes another suitable fluidic guide that is in the form of bands of a barrier substance material (e.g., phase change material) deposited on the topsheet along at least a portion of the periphery of the article. Still another suitable fluid guide may include a permeable sheet (e.g., nonwoven web) adsorbed with an amphiphilic protein (e.g., milk protein) to define a gradient distribution of an amphiphilic protein coating along at least one dimension of the permeable sheet. This provides controlled wettability along at least one dimension of the permeable, liquid flow control material. Such materials are described in more detail in U.S. Pat. No. 5,912,194 to Everhart, et al., which is incorporated herein in its entirety by reference thereto for all purposes. In yet another embodiment, the fluid guide may be a nonwoven web having a high basis weight and/or high denier, such as described in U.S. Pat. No. 4,892,534 to Datta, et al., which is incorporated herein in its entirety by reference thereto for all purposes. For example, the basis weight may range from about 0.5 to 1.0 ounces per square yard, and in some embodiments, from about 0.7 to 1.0 ounces per square yard, and the denier may range from about 3 to about 15, and in some embodiments, from about 4 to about 12. Such high basis weight and high denier webs contain large passageways that extend downward through the thickness of the web and have the ability to draw a greater quantity of bodily fluid away from the visible surface, thereby actively masking visible stains. The fluid guides may be employed in the center and/or periphery of the article as desired.

A chemical treatment may also be employed to alter the color of the bodily fluid should any leakage occur. In one embodiment, for example, the treatment may be a decolorizing composition that agglutinates (agglomerates) red blood cells in blood and menses and limits the extent that the red color of menses is visible. One such composition includes a surfactant, such as described in U.S. Pat. No. 6,350,711 to Potts, et al. which is incorporated herein in its entirety by reference thereto. Particular examples of such surfactants are Pluronic® surfactants (tri-block copolymer surfactant). Another suitable composition that can help agglutinate (agglomerate) the cells includes one or more inorganic salts that contain a polyvalent anion (e.g., divalent, trivalent, etc.), such as sulfate ($SO_4^{2-}$), phosphate ($PO_4^{3-}$), carbonate ($CO_3^{2-}$, oxide ($O^{2-}$, etc., and a monovalent cation, such as sodium ($Na^+$), potassium ($K^+$), lithium ($Li^+$), ammonium ($NH_4^+$), etc. Alkali metal cations are particularly desirable. Specific examples of salts formed from such ions include, for instance, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may be particularly effective in facilitating physical separation of red blood cells. For instance, a mixture of disodium sulfate ($Na_2SO_4$) and monopotassium phosphate ($KH_2PO_4$) may be employed.

Besides agglutinating agents, the decolorizing composition may also alter the chemical structure of hemoglobin to change its color. Examples of such compositions are described in U.S. Patent Application Publication No. 2009/0062764 to MacDonald, et al., which is also incorporated herein in its entirety by reference thereto. More particularly, the composition includes an oxidizing agent that is generally capable of oxidizing hemoglobin or other substances responsible for an unwanted color of the bodily exudates. Suitable oxidizing agents may include, for instance, peroxygen bleaches (e.g., hydrogen peroxide, percarbonates, persulphates, perborates, peroxyacids, alkyl hydroperoxides, peroxides, diacyl peroxides, ozonides, supereoxides, oxo-ozonides, and periodates); hydroperoxides (e.g., tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide); peroxides (e.g., lithium peroxide, sodium peroxide, potassium peroxide, ammonium peroxide, calcium peroxide, rubidium peroxide, cesium peroxide, strontium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, and nickel peroxide); perborates (e.g., sodium perborate, potassium perborate, and ammonium perborate); persulphates (e.g., sodium persulphate, potassiumdipersulphate, and potassium persulphate); and so forth. Other suitable oxidizing agents are omega-3 and -6 fatty acids, such as linoleic acid, α-linoleic acid, arachidonic acid, eicosapentaenoic acid, docosahexaenoic acid, eicosadienoinc acid, eicosatrienoic acid; etc.

The decolorizing composition may be applied to any liquid-permeable layer of the absorbent article where it can contact aqueous fluids exuded by the body (e.g., menses), such as the topsheet, fluid distribution layer, cover, absorbent core, intake layer, and so forth. In one embodiment, the decolorizing composition may cover only a portion of the surface to ensure that the layer is still capable of retaining sufficient absorbent properties. In certain embodiments, it may be desired that the decolorizing composition is positioned closer to the absorbent core to minimize potential leakage. In addition to being applied to the absorbent core, other configurations may also be employed in the present invention. For example, an additional layer (not shown) may be applied with the decolorizing composition that is in contact with the absorbent core. The additional layer may be formed from a variety of different porous materials, such as a perforated film, nonwoven web (e.g., cellulosic web, spunbond web, meltblown web, etc.), foams, etc. In one embodiment, the additional layer may be in the form of a hollow enclosure (e.g., sachet, bag, etc.) that is folded so that it partially or completely surrounds the absorbent core. The decolorizing composition may be disposed within this enclosure so that it remains sealed therein prior to use. In another embodiment, however, the additional layer may be the intake layer. Typically, the decolorizing composition is disposed on a surface facing away from the absorbent core; however, it should also be understood that the decolorizing composition may be positioned on any other surface, such as between the additional layer and the absorbent core.

If desired, the absorbent article of the present invention may also be employed in conjunction with a disposable or reusable garment that is specifically tailored to fit with the absorbent article of the present invention. One example of such an undergarment/absorbent article system is described in U.S. Pat. No. 6,547,774 to Ono, et al., which is incorporated herein in its entirety by reference thereto for all purposes.

As a result of the combination of features employed in the present invention, an absorbent article may thus be formed that exhibits a reduced likelihood of leakage during use. This may be evident throughout the entire use of article, including upon an initial insult of a fluid and subsequently when the article has already absorbed a certain amount of fluid. More particularly, in certain embodiments, embossments and/or apertures may be employed that help facilitate the rapid intake of fluids that can occur during an initial insult. Nevertheless, even as the article fills with fluid and a portion of the absorptive capacity is depleted, the raised topsheet area(s) created by the fluid-shrinkable members of the present invention can still form a barrier to the leakage of fluids from the center of the article towards its edges, thereby further minimizing the likelihood of leakage.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article that generally extends in a plane defined by a longitudinal direction and transverse direction, wherein the article comprises:
   a base pad that contains a baffle and an absorbent core;
   a topsheet that overlies the base pad so that the absorbent core is positioned between the topsheet and the baffle, wherein the topsheet extends in the longitudinal direction to define a distal end and an opposing proximal end, wherein a cut is made in the topsheet to form a separate portion that defines the proximal end, wherein the topsheet is joined to the base pad in a manner such that at least a central portion of the proximal end remains generally unbonded thereto, wherein peripheral portions of the proximal end taper outwardly from the central portion, wherein the central portion raises upwardly and in a longitudinal direction towards a center of the absorbent article to create a raised barrier upon contact with bodily fluid; and
   a fluid-shrinkable member that extends in the longitudinal direction so that at least a portion of the fluid-shrinkable member is located adjacent to the proximal end of the topsheet.

2. The absorbent article of claim 1, wherein the fluid-shrinkable member is in the form of a string.

3. The absorbent article of claim 1, wherein the peripheral portions are joined to the base pad.

4. The absorbent article of claim 1, wherein the topsheet defines an inner region positioned between laterally spaced first and second outer regions, and wherein the fluid-shrinkable member is located adjacent to the inner region, the first outer region, the second outer region, or a combination thereof.

5. The absorbent article of claim 4, wherein the first outer region is folded so that a first portion of the topsheet is disposed above a second portion of the topsheet to define a pocket, and wherein the fluid-shrinkable member is disposed within the pocket.

6. The absorbent article of claim 4, wherein the article comprises a plurality of fluid-shrinkable members, at least a portion of the members being located adjacent to the inner region, the first outer region, the second outer region, or a combination thereof.

7. The absorbent article of claim 1, wherein the topsheet is formed from a center section positioned between a first side section and a second side section, and wherein the first side section is folded so that a first portion of the side section is disposed above a second portion of the side section to define a pocket, and wherein the fluid-shrinkable member is disposed within the pocket.

8. The absorbent article of claim 7, wherein the first portion of the side section is wrapped around the center section.

9. The absorbent article of claim 1, further comprising a fluid distribution layer positioned between the topsheet and the base pad.

10. The absorbent article of claim 9, wherein the fluid-shrinkable member is positioned between and bonded to the topsheet and the fluid distribution layer.

11. The absorbent article of claim 1, wherein the base pad comprises a liquid-permeable cover that is positioned between the topsheet and the absorbent core.

12. The absorbent article of claim 1, wherein the length of the topsheet is less than the length of the baffle.

13. The absorbent article of claim 1, wherein the length of the topsheet is approximately the same as the length of the baffle.

14. The absorbent article of claim 1, wherein contraction of the fluid-shrinkable member is capable of raising the proximal end of the topsheet outwardly from the plane defined by the longitudinal direction and transverse direction of the article.

15. The absorbent article of claim 1, wherein at least a portion of the fluid-shrinkable member is also located adjacent to the distal end of the topsheet.

16. The absorbent article of claim 1, further comprising an additional fluid-shrinkable member that extends in the longitudinal direction so that at least a portion of the additional fluid-shrinkable member is located adjacent to the distal end of the topsheet.

17. A method for forming an absorbent article that generally extends in a plane defined by a longitudinal direction and transverse direction, wherein the article comprises a base pad that contains a baffle and an absorbent core, a fluid-shrinkable member, and a topsheet that extends in the longitudinal direction to define a distal end and a proximal end, the method comprising:
   positioning the fluid-shrinkable member adjacent to the base pad, wherein the fluid-shrinkable member extends in the longitudinal direction; and
   joining the topsheet to the base pad so that the fluid-shrinkable member is positioned between the topsheet and the base pad, wherein a cut is made in the topsheet to form a separate portion that defines the proximal end, wherein at least a central portion of the proximal end of the topsheet remains generally unbonded to the base pad, wherein peripheral portions of the proximal end taper outwardly from the central portion, wherein the central portion raises upwardly and in a longitudinal direction towards a center of the absorbent article to create a raised barrier upon contact with bodily fluid, further wherein at least a portion of the fluid-shrinkable member is located adjacent to the proximal end of the topsheet.

18. An absorbent article that generally extends in a plane defined by a longitudinal direction and transverse direction, wherein the article comprises:
   a base pad that contains a baffle and an absorbent core;
   a topsheet that overlies the base pad so that the absorbent core is positioned between the topsheet and the baffle, wherein the topsheet defines an inner region positioned between laterally spaced first and second outer regions, and further wherein the topsheet extends in the longitudinal direction to define a distal end and an opposing proximal end, wherein the topsheet is joined to the base pad in a manner such that at least a central portion of the proximal end remains generally unbonded thereto, wherein peripheral portions of the proximal end taper outwardly from the central portion, wherein the central portion raises upwardly and in a longitudinal direction towards a center of the absorbent article to create a raised barrier upon contact with bodily fluid, wherein the length of the topsheet is less than the length of the baffle; and a fluid-shrinkable member that extends in the longitudinal direction so that at least a portion of the fluid-shrinkable member is located adjacent to the proximal end of the topsheet.

19. An absorbent article that generally extends in a plane defined by a longitudinal direction and transverse direction, wherein the article comprises:

a base pad that contains a baffle and an absorbent core;

a topsheet that overlies the base pad so that the absorbent core is positioned between the topsheet and the baffle, wherein the topsheet extends in the longitudinal direction to define a distal end and an opposing proximal end, wherein the topsheet is joined to the base pad in a manner such that at least a central portion of the proximal end remains generally unbonded thereto, wherein peripheral portions of the proximal end taper outwardly from the central portion, wherein the central portion raises upwardly and in a longitudinal direction towards a center of the absorbent article to create a raised barrier upon contact with bodily fluid; and a fluid-shrinkable member that extends in the longitudinal direction so that at least a portion of the fluid-shrinkable member is located adjacent to the proximal end of the topsheet, wherein the topsheet defines an inner region positioned between laterally spaced first and second outer regions, wherein the first and second outer regions are each bent outwardly along a fold line, wherein the fold line is located towards a center of the absorbent article.

20. The absorbent article of claim 19, wherein the proximal end of the topsheet is unbonded to the absorbent article.

\* \* \* \* \*